United States Patent [19]

Rajan et al.

[11] Patent Number: 4,467,106
[45] Date of Patent: Aug. 21, 1984

[54] POLYETHER/POLYESTER GLYCOL PROCESS

[75] Inventors: Sundar J. Rajan, Ferndale, Mich.; Edmund F. Perozzi, Crestwood, Mo.

[73] Assignee: Ethyl Corporation, Richmond, Va.

[21] Appl. No.: 368,741

[22] Filed: Apr. 15, 1982

[51] Int. Cl.$^3$ ............................................. C07C 69/88
[52] U.S. Cl. ....................... 560/72; 560/26; 560/25; 560/29; 560/32; 560/75; 560/126; 560/157; 560/163; 560/188
[58] Field of Search .................. 560/72, 188, 25, 26, 560/29, 32, 75, 126, 157, 163

[56] References Cited

U.S. PATENT DOCUMENTS 3,374,277  3/1968  Vandenberg ..................... 260/615

FOREIGN PATENT DOCUMENTS 713296  10/1968  Belgium .

OTHER PUBLICATIONS

Chemical Communications, p. 1578, (1968).
Journal of Catalysis, 27, pp. 389–396, (1972).
Chemical Tech., pp. 600–605, (1971).

*Primary Examiner*—Paul J. Killos
*Attorney, Agent, or Firm*—Donald L. Johnson; John F. Sieberth; John F. Hunt

[57] ABSTRACT

A process for making polyether/polyester glycols and the products formed thereby. Polyether/polyester glycols having a molecular weight of about 200 to 2,200 are formed by heating any of various glycols at about 150° to 250° C. under carbon monoxide pressure in the presence of a halide promoter. Preferably, iodide or bromide and a transition metal-containing catalyst are used to produce polyether/polyester glycols having a molecular weight in the range of 900 to 1,200.

26 Claims, No Drawings

POLYETHER/POLYESTER GLYCOL PROCESS

BACKGROUND OF THE INVENTION

I. Field of the Invention

This invention relates to polymers in general and a process for forming polyether/polyester glycols in particular. This invention also relates to polyether/polyester glycols produced by the inventive process as well as the promoters and catalysts used therefor.

II. Description of the Prior Art

Polyether glycols have been prepared in the past by various methods. Most of the prior art methods required expensive starting materials, catalysts, and process conditions. Polyether glycols are suitable components for polymerization reactions with di or polyisocyanates to form polyurethanes having certain physical properties and characteristics such as good tensile strength. A need exists for varied types of polyether glycols so as to be able to produce polyurethane with enhanced physical and mechanical properties. Especially needed are polyether glycols in the molecular weight range of 900 to 1,800. Also needed is a reliable and simple process for forming such polyether glycols.

Vandenberg, in U.S. Pat. No. 3,374,277 describes a process for the production of very high molecular weight dihydroxy polyethers. Also disclosed by Vandenberg is a separate cleavage step to product polyethers of a more usable molecular weight. The process of Vandenberg is, however, more complicated than the one-step procedure of the present invention.

SUMMARY OF THE INVENTION

The present invention is a process for forming polyether/polyester glycols and the intermediate molecular weight polymers formed thereby. Also, new polyurethanes may be formed by reaction of these new polymers with di or polyisocyanates.

The process comprises heating a glycol at about 150°–250° C. under about 500 to 2,000 psi wherein the pressure is from a gas containing at least about 5% by weight carbon monoxide, preferably substantially pure carbon monoxide. The glycol is heated in the presence of a halide promoter for about four hours or longer. Preferably, the polymerization reaction proceeds in the presence of a transition metal-containing catalyst to yield polyether/polyester glycols of molecular weight in the range 900 to 1,200.

The process forms polyether/polyester glycols of the formula $$HO+(-RCO-)_m(-RO-)_n+ROH$$
$$\phantom{HO+(-R}O\phantom{CO-)_m}$$

wherein m is at least 1, n is at least 1, and m+n is 2 to about 20, wherein the ester groups (m) and ether groups (n) are in any order within the structure (brackets). The molecular weight is about 200 to 2,000, and each R is alkyl, aryl, and the like.

The preferred halide promoter is iodide or bromide furnished from hydrogen iodide, methyl iodide, iodine, ethylbromide, ethylenedibromide, and the like.

Any of various glycols may be used as starting materials. Branched or straight chain alkyls, aryls, alkaryls, aralkyls, cycloalkyls, and mixtures thereof are examples of suitable types of glycols for the invention. These include neopentyl glycol (2,2-dimethyl-1,3-propanediol), cyclohexanedimethanol, 1,6-hexanediol, 1,3-propanediol, and the like. Neopentyl glycol and 1,6-hexanediol are preferred starting materials because the polyether/polyester glycols produced therefrom according to the process of the present invention are in the desirable molecular weight range of 1,000 to 2,000.

Preferably, any of various metal-containing catalysts are also used in the process of this invention. The metals include generally those of the transition elements of the periodic table. Thus, all of rhodium, ruthenium, cobalt, platinum, palladium, osmium, nickel, iron, and copper are suitable materials.

The catalyst may be a compound such as ruthenium oxide, rhodium oxide, cobalt chloride, cobalt oxide, similar compounds, and mixtures thereof. Also available for use with the invention are the rhodium complex catalysts such as [Rh(CO$_2$Cl$_2$]$_2$ and Rh(PO$_3$)$_2$(CO)Cl.

The process of the present invention is conveniently carried out in the presence of about 10–50% halide promoter preferably a halide promoter based on the weight of reactants. Similarly, the process is also conveniently and preferably carried out in the presence of about 0.1–10% metal-containing catalysts such as ruthenium oxide.

A carbon monoxide gas, preferably substantially 100% carbon monoxide is used to pressurize the reaction, thereby increasing the reaction rate. Although the reaction pressure may vary, 500 to 2,000 psi is an acceptable range for most of the polymerization reactions of the present invention, with 1,000 psi being preferred in most cases.

Suitable molecular weight polyether/polyester glycols in the molecular weight range of 200 to 2,200, preferably about 900 to 1,200 are produced by the process of this invention when conducted at a temperature of about 150° to 250° C. These polyether/polyester glycols are valuable reactants in the formation of polyurethanes having desirable physical properties as elastomers and other products.

A polyether/polyester glycol such as one of the formula described above $$HO+(-RCO-)_m(-RO-)_n+ROH \qquad (I)$$
$$\phantom{HO+(-R}O\phantom{CO-)_m}$$

is reacted with a di or polyisocyanate to form a prepolymer. The prepolymer is then reacted with a chain extender such as 1,4-butanediol or a diamine chain extender to form a polyurethane.

It is, therefore, an object of this invention to provide a process for making polyether/polyester glycols in the molecular weight range of 200 to 2,200, preferably about 900 to 1,200.

It is also an object of the present invention to provide new polyether/polyester glycols suitable for various uses including formation of polyurethanes from isocyanates and chain extenders, etc.

DESCRIPTION OF THE PREFERRED EMBODIMENTS

The process of the invention was carried out many times, varying the several parameters to obtain the novel polyether/polyester glycols of the invention in the variable molecular weight range of 200 to 2,200. It has been shown that the parameters of the invention may be varied to obtain the especially desirable molecular weight polymers in the range 900 to 1,200. The following examples are illustrative.

EXAMPLE 1

To a glass liner for a rocking autoclave were added 25 gms of 1,6-hexanediol, 1.4 mls of methyl iodide and 0.3 gms ruthenium oxide. The glass liner was stoppered, introduced into the autoclave and pressurized to about 2,000 psi with carbon monoxide. The autoclave was then heated to 190° C. and kept at that temperature for about two hours and 45 minutes. After cooling the liner and contents to ambient temperature, the pressure was released. The reaction product was diluted with diethylether, washed with water, and dried using sodium sulfate. The product was then concentrated under reduced pressure.

The obtained yield was 78% of theory and the molecular weight, determined by hydroxyl number and gel permeation chromatography methods was 2,170.

This polyether/polyester glycol is suitable for making polyurethanes having good physical properties.

Infrared spectroscopy indicated the presence of ether linkages; acid and ester numbers were 1.0 and 129 respectively.

This product may contain small amounts of iodine in the polymer structure that may be readily removed by treatment with acid.

EXAMPLE 2

The procedure followed was the same as that described for Example 1 except that the initial carbon monoxide pressure was 1,000 psi. The obtained yield of the polymer product was 68% and the product molecular weight was estimated by hydroxyl number method only to be 434.

EXAMPLE 3

The procedure followed was as for Example 1 except that methyl iodide was replaced by 5.4 gms of iodine. A 60% yield was obtained. The polymer molecular weight was determined by hydroxyl number method to be 693.

EXAMPLE 4

Using the procedure of Example 1 with a methyl iodide promoter, in the absence of a catalyst, a 68% yield was obtained for a polymer having a molecular weight of 386.

EXAMPLE 5

The procedure of Example 1 was carried out in the absence of ruthenium oxide at 290° C. A polymer of molecular weight 727 was obtained in 50% yield.

EXAMPLE 6

The procedure of Example 1 was repeated, allowing the reaction to proceed for 15 hours. A polymer of molecular weight 11,220 was obtained in 75% yield. This example shows that excessive heating may allow formation of molecules larger than the desired molecular weight.

EXAMPLE 7

The procedure of Example 1 was followed using neopentyl glycol (2,2-dimethyl-1,3-propanediol) as a starting material and heating for a total of four hours. A polymer of molecular weight 343 was obtained in 54% yield.

EXAMPLE 8

About 25.0 gms of neopentyl glycol, 1.4 mls of methyl iodide, and 0.3 gms of ruthenium chloride were added to a glass liner for a rocking autoclave. The liner was stoppered and pressurized to about 2,000 psi with carbon monoxide. After heating for about 15 hours at 190° C. a polyether/polyester having a molecular weight of 578 was obtained in 60% yield. The reaction product was purified according to the process described in Example 1.

EXAMPLE 9

The procedure of Example 8 was followed except that a hydrogen iodide promoter and ruthenium oxide catalyst were used and the reaction process was cooled after only four hours. A polyether/polyester having a molecular weight of 587 was obtained in 36% yield.

EXAMPLE 10

The procedure of Example 8 was repeated except that the methyl iodide promoter was present in about 50 mole percent rather than 10 mole percent as with the other example herein. The obtained yield of product was 65% which was a polyether/polyester glycol having a molecular weight of 1,154.

EXAMPLE 11

The procedure followed was the same as that described for Example 1 except that the polyether/polyester glycol was prepared from cyclohexane dimethanol (1,4-di-hydroxymethyl cyclohexane) using ruthenium chloride as the metal-containing catalyst. The reaction mixture was cooled after three hours of heating to obtain a 43% yield of a polyether/polyester glycol having a molecular weight of 372 (hydroxyl number method).

EXAMPLE 12

The procedure used was the same as that described for Example 1 except that the polyether/polyester was prepared from neopentyl glycol using a rhodium oxide catalyst and heating for a total of four hours. A 42% yield was obtained. The molecular weight of the product was determined by hydroxyl number method to be 583.

In the above examples, further analytical methods may be used to more precisely determine the molecular weights of the polyether/polyester glycol products.

The reaction conditions, glycol starting material, halide promoter, and other features may be varied without departing from the scope or spirit of the invention as defined by the appended claims.

We claim:

1. A process for forming a polyether/polyester glycol comprising heating a glycol to about 150°–250° C. under pressure of a gas containing at least about 5% by weight carbon monoxide at about 500–2,000 psi in the presence of a halide promoter and a ruthenium catalyst, said glycol being selected from the group consisting of straight chain alkylene, branched alkylene, and cycloalkylene glycols, and recovering therefrom an intermediate molecular weight polyether/polyester glycol.

2. The process of claim 1 wherein said catalyst is $RuO_2$.

3. The process of claim 1 wherein said catalyst is $RuCl_3$.

4. The process of claim 1 wherein said halide promoter is an iodide.

5. The process of claim 1 wherein said iodide promoter is HI.

6. The process of claim 9 wherein said iodide promoter is CH$_3$I.

7. The process of claim 9 wherein said iodide promoter is I$_2$.

8. The process of claim 1 wherein said halide is C$_2$H$_5$Br, C$_2$H$_4$Br$_2$, or other bromide promoters.

9. The process of claim 1 wherein said halide promoter is present in a concentration of about 10-50% by weight of the reactants.

10. The process of claim 1 wherein said catalyst is present in the concentration of about 0.1% to 10% by weight of the reactants.

11. The process of claim 1 wherein the pressure of the gas is about 1,000 psi.

12. The process of claim 1 wherein the heating is carried out at about 190° C.

13. The process of claim 1 wherein said gas is substantially all carbon monoxide.

14. The process of claim 1 wherein said glycol is neopentyl glycol.

15. The process of claim 1 wherein said glycol is cyclohexanedimethanol.

16. The process of claim 1 wherein said glycol is 1,6-hexanediol.

17. The process of claim 1 wherein said glycol is 1,3-propanediol.

18. A polymer formed by the process of claim 1 and having the formula

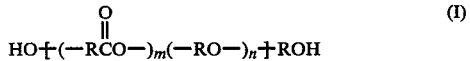 (I)

where m is at least 1, n is at least 1, and m+n is 2 to about 20, wherein the ester groups and ether groups are in any order within the structure, the molecular weight is about 200 to 2,200, and each R is alkylene or cycloalkylene.

19. A polymer formed by the process of claim 1 having the formula

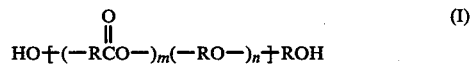 (I)

wherein m is at least 1, n is at least 1, and m+n is 2 to about 20, wherein the ester groups and ether groups are in any order within the structure, the molecular weight is about 900 to 1,200 and each R is alkylene or cycloalkylene.

20. A polyether/polyester glycol of the formula

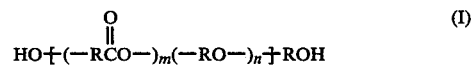 (I)

where m is at least 1, n is at least 1, and m+n is 2 to about 20, wherein the ester groups and ether groups are in any order within the structure, the molecular weight is about 200 to 2,200, and each R is alkylene or cycloalkylene.

21. A polymer of claim 20 wherein R is the divalent neopentyl.

22. A polymer of claim 20 wherein R is —(CH$_2$)$_6$—.

23. A polymer of claim 20 wherein R is

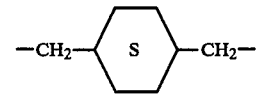

24. A polymer of claim 20 wherein R is propylene.

25. The process of claim 1 wherein said heating is carried out for about 4 to 24 hours.

26. A polyurethane formed by the reaction of a di or polyisocyanate and a polyether/polyester glycol of claim 20.

* * * * *

UNITED STATES PATENT AND TRADEMARK OFFICE
CERTIFICATE OF CORRECTION

PATENT NO. : 4,467,106
DATED : August 21, 1984
INVENTOR(S) : Sundar J. Rajan et al.

It is certified that error appears in the above-identified patent and that said Letters Patent is hereby corrected as shown below:

Column 1, line 59, "200 to 2,000" should read -- 200 to 2,200 --.
Column 5, line 3, "Claim 9" should read -- Claim 4 --.
Column 5, line 5, "Claim 9" should read -- Claim 4 --.
Column 6, line 25, "neopentyl" should read -- neopentyl group --.

Signed and Sealed this

Fifth Day of March 1985

[SEAL]

Attest:

DONALD J. QUIGG

*Attesting Officer*    *Acting Commissioner of Patents and Trademarks*